United States Patent

Michel

[11] Patent Number: 6,106,501
[45] Date of Patent: Aug. 22, 2000

[54] INJECTION DEVICE

[75] Inventor: Peter Michel, Burgdorf, Switzerland

[73] Assignee: Disetronic Licensing AG, Switzerland

[21] Appl. No.: 08/860,829

[22] PCT Filed: Nov. 9, 1995

[86] PCT No.: PCT/CH95/00262

§ 371 Date: Sep. 5, 1997

§ 102(e) Date: Sep. 5, 1997

[87] PCT Pub. No.: WO97/17096

PCT Pub. Date: May 15, 1997

[51] Int. Cl.[7] ........................ A61M 5/00
[52] U.S. Cl. ............ 604/208; 604/224; 604/232
[58] Field of Search ................ 604/207, 208, 604/232, 194, 195, 221, 224, 234, 210; 222/287, 309, 396, 634

[56] References Cited

U.S. PATENT DOCUMENTS

| 4,865,591 | 9/1989 | Sams .................................. 604/208 X |
| 4,973,318 | 11/1990 | Holm et al. .......................... 604/208 |
| 5,114,406 | 5/1992 | Gabriel et al. ...................... 604/232 X |
| 5,279,585 | 1/1994 | Balkwill ............................ 604/232 X |
| 5,549,575 | 8/1996 | Giambattista et al. ................ 604/232 |
| 5,591,136 | 1/1997 | Gabriel .............................. 604/211 |

*Primary Examiner*—Ronald Stright
*Assistant Examiner*—A. T. Nguyen
*Attorney, Agent, or Firm*—Dorsey & Whitney LLP

[57] ABSTRACT

An injection device is described which is lockable in its end position in such a manner that the reliability of storing or transporting it with a carpule attached is improved in comparison with devices according to the prior art. It is comprised of fewer components than comparable devices, with these components being easier to manufacture so that production costs are low. The injection device is used for medical purposes.

16 Claims, 3 Drawing Sheets

INJECTION DEVICE

RELATED APPLICATIONS

This application claims the priority of PCT application No. PCT/CH95/00262, filed Nov. 9, 1995, which is incorporated herein by reference.

BACKGROUND OF THE INVENTION

1. Field of the Invention

The present invention relates to a device for repeatedly injecting dosages of a liquid medicament from a container for liquids, especially a carpule (=injection ampoule), equipped with a piston, said container being attachable to or detachable from a manually drivable transmission incorporated into a transmission sleeve, said transmission comprising a drive member comprised of a guide button and a carrier sleeve firmly attached thereto, said drive member being disposed rotatably and shiftably in the advance direction of the piston in the transmission sleeve, a driven member comprised of a threaded rod and a flange, said driven member being shiftable in the advance direction of the piston and being carriable over a certain distance under the influence of the drive member executing longitudinal shifts, a transmission element being screwably disposed on the threaded rod and having the effect of the driven member being carried along by the drive member, a compression spring acting between the transmission sleeve and the carrier sleeve, in which the drive member is lockable by a locking device, the threaded rod of the driven member is disposed nonrotatably and shiftable in the longitudinal direction in the transmission sleeve, and the transmission element is rotatable but attached shiftably in the longitudinal direction to the drive member.

2. Description of the Prior Art

Such injection devices have been known for some time, for example a device described in EP-0 245 312 B1 which must be regarded as the closest prior art. It has the purpose of injecting respectively selectable amounts of liquid from a container for liquids equipped with a piston, especially a carpule (=injection ampoule).

Said carpule in a carpule holder is attachable to or detachable from a manually drivable transmission. The transmission is incorporated into a transmission sleeve. In addition to other parts, it comprises

- a drive member comprised of a guide button and a carrier sleeve firmly attached thereto, said drive member being disposed rotatably and shiftably in the advance direction of the piston in the transmission sleeve,
- a driven member comprised of a threaded rod and a flange, said driven member being shiftable in the advance direction of the piston and being carriable over a certain distance under the influence of the drive member executing longitudinal shifts,
- a transmission element being screwably disposed on the threaded rod,
- a compression spring acting between the transmission sleeve and the carrier sleeve.

While being operated, the injection device may be in the following positions:

- a home position, where the drive member is at its furthest possible distance from the piston and the transmission element is close to the piston,
- an intermediate position where the drive member remains in its position, but the transmission element, depending on the amount of liquid to be injected, is further away from the piston than in its home position,
- a final position where the drive member is closer to the piston and the driven member has protruded further from the transmission than in the home or intermediate position and has penetrated into the carpule which causes injection of the selected amount of liquid.

The final position reverts to the home position by itself. The transmission is not locked in any of the three positions so that it may be exposed to influences during storage or transport of the injection device which may cause a change in the amount of liquid in the carpule or even permit the entry of air into the carpule. In addition, it has many components, some of which are not very easy to manufacture.

SUMMARY OF THE INVENTION

The invention is based on the objective to provide an injection device which is self-lockable in at least one position which is then regarded as the final position.

The subject matter of claim 1 is the solution of this objective according to the invention. Preferred additional embodiments of the invention are described in detail in the ensuing claims. The injection device described in these claims can be comprised of fewer components than comparable devices with the components being easier to manufacture than known injection devices.

BRIEF DESCRIPTION OF THE DRAWINGS

In the following, one embodiment of the invention will be illustrated in detail on the basis of the drawing, wherein.

DESCRIPTION OF THE PREFERRED EMBODIMENTS

Figure 1:
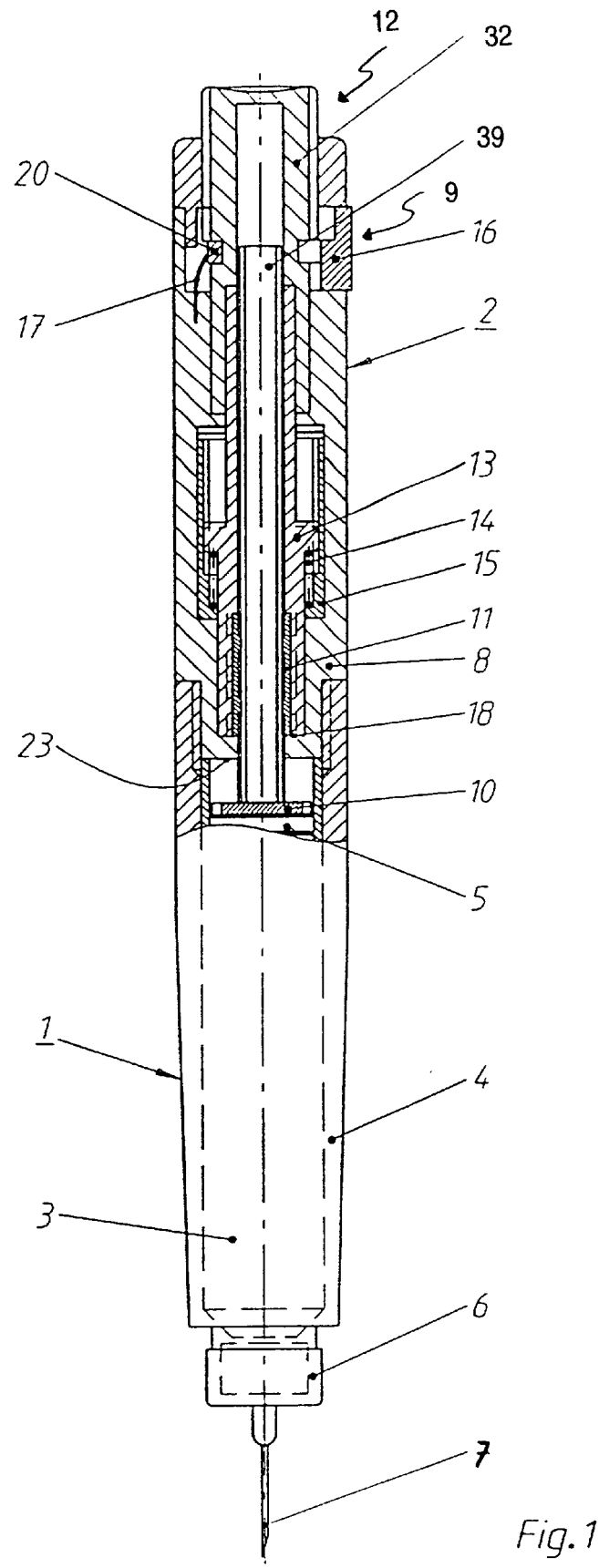
FIG. 1 shows an axial longitudinal section through the injection device according to the invention in one final position.
Figure 2:
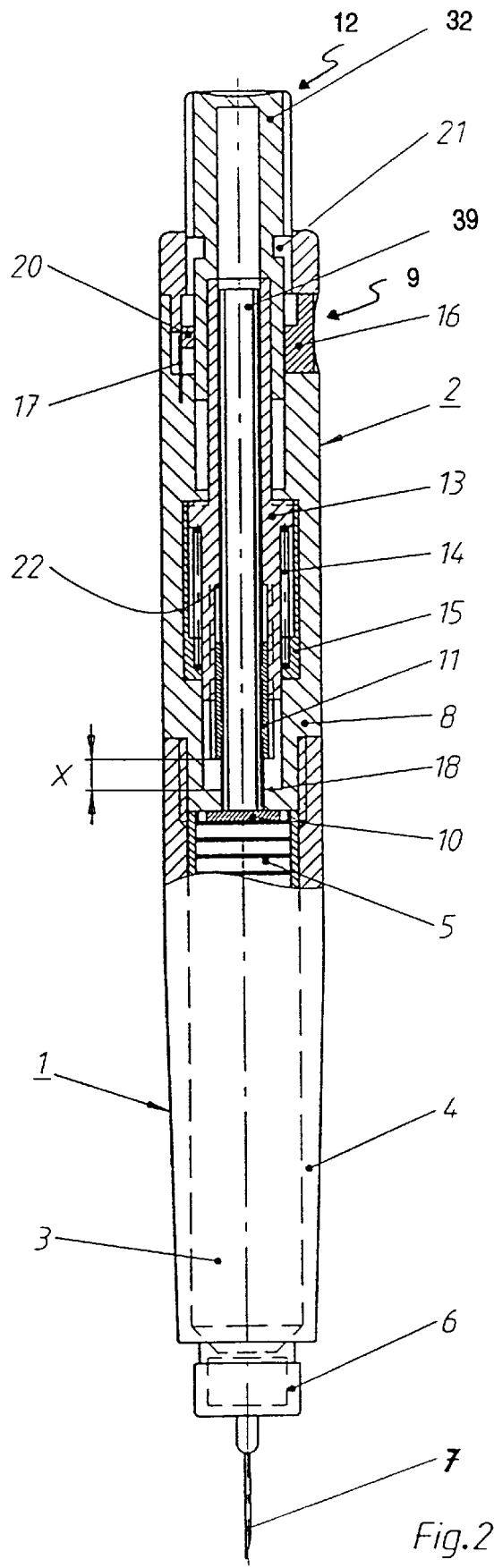
FIG. 2 shows the same in a home position.
Figure 3:
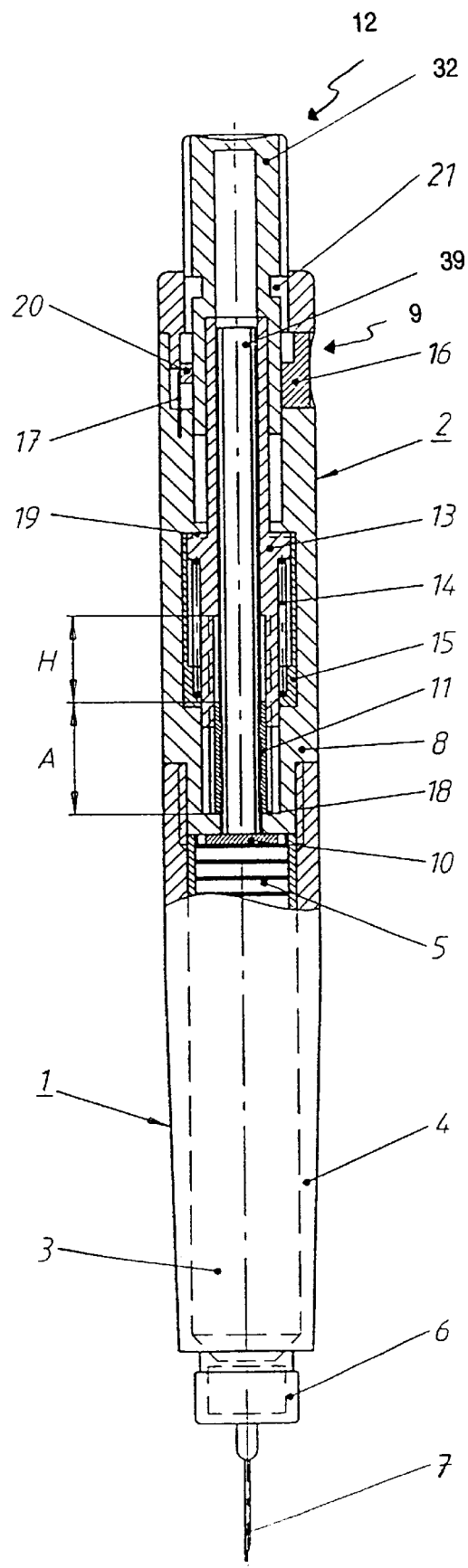
FIG. 3 shows the same in an intermediate position.

The injection device shown in FIGS. 1 to 3 has a carpule part 1 and a transmission 2 which is easily attachable and detachable, for example by means of a thread or a bayonet socket.

The carpule part 2 comprises a container 3 for liquids, hereinafter called "carpule" 3, filled with the liquid to be injected, a carpule holder 4, a piston 5 which is in contact with the liquid at all times and displaces the liquid to be injected during the act of injecting, a needle holder 6 and a needle 7 from which the liquid to be injected is ejected.

The transmission 2 is incorporated in a transmission sleeve 8. It comprises

- a drive member 12, comprised of a guide button 32 and a carrier sleeve 13 firmly attached thereto, said drive member being disposed rotatably and shiftably in the advance direction of the piston 5 in the transmission sleeve 8,
- a driven member 9, comprised of a threaded rod 39 and a flange 10, said driven member being shiftable in the advance direction of the piston 5 and being carriable over a certain distance under the influence of the drive member 12, 13 executing longitudinal shifts,
- a transmission element 11 being screwably disposed on the threaded rod 9 and having the effect of the driven member 9, 10 being carried along by the drive member 12, 13, a compression spring 14 held by a spring sleeve 15 and acting between the transmission sleeve 8 and the carrier sleeve 13.

The injection device according to the invention has the following constructive features:

A locking device 16, 17, 20, 21 engages with the drive member 12, 13.

The threaded rod 9 of the driven member 9, 10 is disposed non-rotatably but shiftably in the longitudinal direction in the transmission sleeve 8.

The transmission element 11 is non-rotatable but attached shiftably in the longitudinal direction to the drive member 12, 13.

The flange 10 of the drive member 9, 10 is contiguous to the piston 5 being in contact with the liquid as long as the carpule 3 is connected to the transmission 2.

It has the properties described below:

At the end of each injection, the transmission 2 is in a locked end position (FIG. 1) in which end position (FIG. 1) it may also be stored and transported. In this end position (FIG. 1), the drive member 12, 13 protrudes relative to the transmission sleeve 8 so far in the advance direction towards the piston 5 that the lock 16, 17, 20, 21 between the transmission sleeve 8 and the drive member 12, 13 engages and secures it against rotation and shifting in the longitudinal direction. In addition, the transmission element 11 is in contact with a first stopper 18 on the transmission sleeve 8 in the direction of the piston 5 which limits said transmission sleeve in the direction of the piston.

When the lock 16, 17, 20, 21 is engaged, the drive member 12, 13 is neither rotatable nor shiftable. Therefore, it is not possible to operate the injection device—not even intentionally—while it is in the final position (FIG. 1) and thus it cannot lose any liquid. This distinguishes it from the injection devices known previously.

The lock 16, 17, 20, 21, for example, consists of a locking ring 16 encircling the drive member 12, 13 and a cam 20 connected therewith. Said cam is positioned in the transmission sleeve 8 and when pressed by a spring 17 engages in the drive member 12, 13 in the final position. Said cam can only be released from the groove 21 by pressing the locking ring 16 against the spring 17. Once the lock 16, 17, 20, 21 has been released, the drive member 12, 13 is once again rotatable and shiftable and is pushed by the compression spring 14 into the home position (FIG. 2) described below. However, a lock having comparable properties may also be designed in a different manner.

In order to carry out another injection, the transmission 2 is first brought into a home position (FIG. 2). In said home position, the drive member 12, 13 is pushed as far as possible away from the piston 5 opposed to the advance direction of the piston and this is effected by the compression spring 14 which pushes the drive member 12, 13 by a distance H up to a second stopper 19 on the transmission sleeve 8. Said second stopper 19 is, for example, an annular ring on the surface of the inner jacket of the transmission sleeve 8. The transmission element 11 is still contiguous to the first stopper 18 of the transmission sleeve (8) in the direction of the piston 5. The shift from the final position (FIG. 1) to the home position (FIG. 2) is effected by releasing the lock (16, 17, 20, 21) of the transmission sleeve 8 and the drive member 12, 13, said drive member 12, 13 becoming rotatable and shiftable in the longitudinal direction and the compression spring 14 shifting the drive member 12, 13 opposed to the advance direction of the piston (5) into the home position (FIG. 2).

From the home position (FIG. 2), the transmission 2 is brought into an intermediate position (FIG. 3) which is determined by the amount of liquid to be injected with the next injection. In said intermediate position, the lower end of the transmission element 11 is shifted by a distance X relative to the first stopper 18 on the transmission sleeve 8 opposed to the advance direction of the piston 5, said distance X being determined by with I being the amount of liquid to be injected and F being the inner cross sectional area of the carpule.

The shift from the home position (FIG. 2) to the intermediate position (FIG. 3) is effected by rotating the drive member 12, 13 in such a direction that the transmission element 11 which is connected shiftably in the longitudinal direction and rotatable with the drive member 12, 13 is rotated around its axis, the threaded rod 9, in such a manner that it is shifted along said threaded rod 9 opposed to the advance direction of the piston 5 by the distance X.

The transmission element 11 is shiftable to a third stopper 22 on the carrier sleeve 13 at most. Said stopper is positioned against the advance direction of the piston on the inner jacket surface of the drive member at a distance A+H from the first stopper 18, with A being the length of the transmission element (11)

H being the travel distance of the drive member between the final position (FIG. 1) and the home position (FIG. 2).

The following applies for the maximum shift distance H:

$$H \geq X.$$

From the intermediate position (FIG. 3), the transmission is brought into the final position (FIG. 1). During this time the injection procedure is carried out. For this purpose, the drive member 12, 13 is shifted by the distance H in the advance direction of the piston. During this advance shift, the drive member 12, 13 carries the transmission element 11 forward which is positioned at a distance X from the first stopper 18 on the transmission sleeve 8. From that point onwards, the transmission element 11 carries the driven member 9, 10 which is shiftable only the longitudinal direction along by the distance X. During this operation, the flange 10 thereof pushes the piston 5 in the carpule 3 forward so that the amount of liquid I=F×X is displaced on the whole and ejected through the needle 7 (injection). When the drive member 12, 13 has travelled the distance H and the transmission element 11 has travelled the distances X at the same time, the lock 16, 17, 20, 21 engages into the drive member 12, 13. Thus the transmission 2 comes to rest in the final position, the drive member 12, 13 is no longer rotatable or shiftable in the longitudinal direction and the injection device thus protected against a loss of liquid.

After the entire liquid in the carpule 3 has been consumed, the carpule part 1 is detached from the transmission 2 in the home position (FIG. 2). Then the driven member 9, 10 must be pushed back by rotating the drive member 12, 13 in the reverse direction of the shift from the home position (FIG. 2) into the intermediate position (FIG. 3) until the flange 10 comes to rest on the stopper 23 of the transmission sleeve 8.

Advantageously the new carpules 3 to be inserted are filled in such a manner that the piston 5 is pushed forward a little by the flange 10 during incorporation into the injection device and some liquid is ejected from the needle 7. This ensures that no air is injected even during the first injection with the new carpule 3.

The injection devices according to the invention may be equipped with electrical, optical or acoustic means capable of indicating the selected distance X. This may, for example, be a ratchet which acts between the driven member (9, 10) and the transmission sleeve (8).

The injection device according to the invention has a lock 16, 17, 20, 21 which prevents even intentional operation while it is in the final position (FIG. 1). This means that it may be stored and transported more reliably even with the carpule 3 attached than devices according to the prior art. Moreover, it is comprised of fewer components some of which are easier to manufacture so that the required production costs are lower.

I claim:

1. A transmission for an injection device for injecting an amount of liquid from a container equipped with a piston, the container being attachable to and detachable from the transmission, the transmission having home, end and intermediate positions and comprising:

a transmission sleeve having a generally central longitudinal axis;

a drive member comprising a guide button and a carrier sleeve fixedly attached to the guide button, said drive member being disposed rotatably and axially shiftably in the transmission sleeve, a driven member comprising a threaded rod and a flange, said threaded rod disposed nonrotatably and axially shiftably in the transmission sleeve, said driven member being shiftable axially in the transmission sleeve over a distance under the influence of the drive member executing axial shifts, a transmission element being screwably disposed on the threaded rod whereby the driven member is moved axially by the drive member, said transmission element shiftible axially with respect to the drive member, and a lock for locking the transmission in the end position, said lock operatively coupling the transmission sleeve and the drive member, whereby said lock engages and secures said drive member against rotation and axial shifting.

2. The transmission according to claim 1, in which a shift from the end position into the home position is effected by loosening the lock between the transmission sleeve and the drive member, whereby the drive member is then rotatable and axially shiftable into the home position.

3. The transmission according to claim 2, in which the lock comprises a locking ring and a cam positioned in the transmission sleeve and pressed against the drive member by a spring, said cam engaging in a groove on the drive member in the end position and being releasable from said groove by pressing the locking ring.

4. The transmission according to claim 1, wherein the piston has an injection delivering advance direction of movement, and wherein the transmission's move from the intermediate position to the end position is effected by axially shifting the drive member in the advance direction of piston movement, wherein the drive member carries the transmission element in an axial movement over a distance from a first stopper on the transmission sleeve in the advance direction of the piston, and further wherein starting from said distance, the transmission element carries the driven member in an axial shift until the transmission element pushes against the first stopper on the transmission sleeve, whereby a flange associated with the driven member pushes the piston into the container over said distance whereby a selected amount of liquid to be injected is discharged from the container.

5. The transmission according to claim 4, wherein the lock engages the drive member when the transmission element reaches the stopper on the transmission sleeve, whereby the drive member is locked in the end position and may not be rotated or shifted in an axial direction.

6. The transmission according to claim 4, wherein the intermediate position is selectable and wherein when in said intermediate position, an end of the transmission element is positioned a distance X from the first stopper in a direction generally opposite to the advance direction of the piston.

7. The transmission according to claim 6, wherein the distance X is determined by the amount of liquid to be injected divided by the inner cross-sectional area of the container.

8. An injection device for injecting a selectable amount of liquid, said injection device comprising:

a carpule having a piston with an injecting direction of movement;

a manually drivable transmission, said carpule being attachable to and detachable from said transmission, said transmission comprising:

a transmission sleeve, said transmission sleeve generally tubular and having a generally central longitudinal axis;

a drive member comprising a guide button and a carrier sleeve firmly attached to said guide button, said drive member being disposed rotatably and axially shiftably in the transmission sleeve;

a driven flange member comprising a threaded rod and a flange, said driven member being axially shiftable in the transmission sleeve and being carriable over a certain distance under the influence of the drive member executing axial shifts;

a transmission element screwably disposed on the threaded rod, whereby the driven member is carried by the drive member;

a compression spring acting between the transmission sleeve and the carrier sleeve; and a lock operably coupling the transmission sleeve and the drive member for locking the drive member, whereby said lock engages and secures said drive member against rotation and axial shifting.

9. The injection device according to claim 8, wherein the threaded rod is disposed nonrotatably and axial shiftably in the transmission sleeve, and the transmission element is rotatable and attached axially shiftably to the drive member.

10. The injection device according to claim 8, wherein at the end of an injection, the transmission is in a locked end position in which the drive member is positioned near the piston, and wherein in order to prepare another injection the transmission is first moved into a home position wherein the drive member is at a distance from the piston and from said home position is moved into an adjustable intermediate position from which said transmission is moved to the locked end position thereby performing an injection.

11. The injection device according to claim 10, wherein the move from the home position into the intermediate position is accomplished by turning the drive member in such a direction that the transmission element is moved along the threaded rod.

12. The injection device according to claim 10, wherein in the home position the drive member is urged by the compression spring in a direction opposite to the injecting direction of movement of the piston whereby the drive member stops at one stopper associated with the transmission sleeve, and wherein the transmission element remains stopped at another stopper of the transmission sleeve.

13. The injection device according to claim 12, further comprising an indicating means for indicating the selected amount of liquid to be injected, said indicating means consisting of one of the group of electrical, optical or acoustical indicating means for indicating the selected amount of liquid to be injected.

14. The injection device according to claim 13, wherein the indicating means comprises an acoustical means comprising a ratchet operably coupled between the drive member and the transmission sleeve.

15. The injection device according to claim 10, wherein the selected adjustment of the intermediate position determines the amount of liquid to be injected.

16. The injection device according to claim 10, wherein the lock automatically and positively locks the transmission in the locked end position.

* * * * *